(12) United States Patent
Wang (10) Patent No.: US 10,531,786 B2
(45) Date of Patent: Jan. 14, 2020

(54) IN VIVO CAPSULE DEVICE WITH ELECTRODES

(71) Applicant: Capso Vision, Inc, Saratoga, CA (US)

(72) Inventor: Kang-Huai Wang, Saratoga, CA (US)

(73) Assignee: CAPSO VISION INC, Saratoga, CA (US)

( * ) Notice: Subject to any disclaimer, the term of this patent is extended or adjusted under 35 U.S.C. 154(b) by 408 days.

(21) Appl. No.: 15/081,948

(22) Filed: Mar. 28, 2016

(65) Prior Publication Data
US 2016/0206183 A1 Jul. 21, 2016

Related U.S. Application Data

(62) Division of application No. 13/945,598, filed on Jul. 8, 2013, now abandoned.

(60) Provisional application No. 61/683,878, filed on Aug. 16, 2012.

(51) Int. Cl.
*A61B 1/00* (2006.01)
*A61B 1/04* (2006.01)

(52) U.S. Cl.
CPC .......... *A61B 1/00156* (2013.01); *A61B 1/041* (2013.01)

(58) Field of Classification Search
CPC . A61B 1/00043; A61B 1/041; A61B 1/00156; A61B 1/00018; A61B 1/00124; A61B 5/6861; A61N 1/37205
USPC .......................................... 600/101, 117, 118
See application file for complete search history.

(56) References Cited

U.S. PATENT DOCUMENTS

| | | | | |
|---|---|---|---|---|
| 4,286,585 A * | 9/1981 | Ogawa | ................. | A61B 1/0016 250/227.2 |
| 5,833,603 A * | 11/1998 | Kovacs | ............... | A61B 1/00016 600/109 |
| 7,020,531 B1 * | 3/2006 | Colliou | .............. | A61N 1/36007 604/891.1 |
| 7,200,253 B2 * | 4/2007 | Glukhovsky | .......... | A61B 1/041 382/128 |
| 7,983,458 B2 * | 7/2011 | Wang | ................. | A61B 1/00009 348/699 |
| 8,303,490 B2 * | 11/2012 | Kawano | ............. | A61B 1/00156 600/118 |
| 8,512,219 B2 * | 8/2013 | Ferren | ................ | A61B 1/00156 600/12 |
| 8,547,248 B2 * | 10/2013 | Zdeblick | .............. | A61B 5/0028 340/870.28 |

(Continued)

*Primary Examiner* — Timothy J Neal
*Assistant Examiner* — Jae Woo
(74) *Attorney, Agent, or Firm* — Blairtech Solution LLC (57) ABSTRACT

A capsule endoscopic device with movement control is disclosed. The capsule endoscopic device comprises a capsule housing, one or more electrodes disposed fixedly through the capsule housing, a signal generation/signal driver unit, an interface circuit and a switch module. The electrodes apply electrical stimulus to living body tissue in a patient's gastrointestinal track. The signal generation/signal driver unit generates the electrical stimulus for the electrodes. The switch module is coupled to the electrodes, the signal generation/signal driver unit and the interface circuit. Furthermore, the switch module is configured to connect the electrodes to the signal generation/signal driver unit or the interface circuit depending on an operation mode. The switch module, the signal generation/signal driver unit and the interface circuit are inside the capsule housing.

8 Claims, 6 Drawing Sheets

(56) References Cited

U.S. PATENT DOCUMENTS

| | | | | |
|---|---|---|---|---|
| 8,682,440 B2* | 3/2014 | Imran | A61K 38/26 | 607/40 |
| 8,734,429 B2* | 5/2014 | Imran | A61M 5/14244 | 604/145 |
| 2002/0193669 A1* | 12/2002 | Glukhovsky | A61B 5/0031 | 600/302 |
| 2002/0198470 A1* | 12/2002 | Imran | A61B 1/00082 | 600/587 |
| 2003/0023150 A1* | 1/2003 | Yokoi | A61B 1/00016 | 600/300 |
| 2004/0106849 A1* | 6/2004 | Cho | A61B 1/04 | 600/101 |
| 2005/0043587 A1* | 2/2005 | Fujimori | A61B 1/00029 | 600/160 |
| 2005/0159643 A1* | 7/2005 | Zinaty | A61B 1/041 | 600/109 |
| 2005/0183733 A1* | 8/2005 | Kawano | A61B 1/00156 | 128/899 |
| 2008/0035521 A1* | 2/2008 | Takizawa | A61B 1/00144 | 206/534 |
| 2008/0108868 A1* | 5/2008 | Swain | A61B 1/00156 | 600/104 |
| 2008/0279431 A1* | 11/2008 | Kitamura | A61B 1/00009 | 382/128 |
| 2008/0300453 A1* | 12/2008 | Aoki | A61B 1/00156 | 600/103 |
| 2009/0073260 A1* | 3/2009 | Nagase | A61B 1/00009 | 348/68 |
| 2009/0073273 A1* | 3/2009 | Wang | A61B 1/00016 | 348/222.1 |
| 2009/0099500 A1* | 4/2009 | Nitzan | A61N 1/0428 | 604/20 |
| 2009/0137883 A1* | 5/2009 | Chiba | A61B 1/041 | 600/302 |
| 2009/0204181 A1* | 8/2009 | Kawano | A61B 1/00156 | 607/62 |
| 2009/0322865 A1* | 12/2009 | Wang | A61B 1/00009 | 348/68 |
| 2010/0191055 A1* | 7/2010 | Minai | A61B 1/04 | 600/109 |
| 2010/0220179 A1* | 9/2010 | Wang | A61B 1/00009 | 348/68 |
| 2012/0201235 A1* | 8/2012 | Lim | A61B 1/00016 | 370/349 |
| 2013/0002842 A1* | 1/2013 | Das | H04N 7/18 | 348/65 |
| 2013/0053928 A1* | 2/2013 | Gat | A61B 5/6861 | 607/88 |
| 2014/0296666 A1* | 10/2014 | Rabinovitz | A61B 5/1459 | 600/310 |
| 2014/0323804 A1* | 10/2014 | Wilson | A61B 1/00013 | 600/109 |
| 2014/0343358 A1* | 11/2014 | Hameed | A61B 1/053 | 600/109 |

* cited by examiner

Fig. 7

IN VIVO CAPSULE DEVICE WITH ELECTRODES

CROSS REFERENCE TO RELATED APPLICATIONS

The present invention is a divisional application of and claims priority to U.S. patent application, Ser. No. 13/945,598, filed on Jul. 18, 2013, which is a non-provisional patent application and claims priority to U.S. Provisional Application, Ser. No. 61/683,878, filed on Aug. 16, 2012. The present invention is also related to U.S. Provisional Patent Application, Ser. No. 61/657,747, filed on Jun. 9, 2012. The U.S. Patent Application and U.S. Provisional Patent Applications are hereby incorporated by reference in their entireties.

FIELD OF THE INVENTION

The present invention relates to in vivo capsule device. In particular, the present invention relates to multi-purpose electrodes, detection of capsule direction inside the GI tract and the capsule device movement control.

BACKGROUND AND RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Because of the difficulty traversing a convoluted passage, endoscopes cannot reach the majority of the small intestine and special techniques and precautions, that add cost, are required to reach the entirety of the colon. Capsule endoscope is an alternative in vivo image sensor that addresses many of these problems. A camera is housed in a swallowable capsule, along with a radio transmitter for transmitting data, primarily comprising images recorded by the digital camera, to a base-station receiver or transceiver and data recorder outside the body. Another autonomous capsule camera system with on-board data storage was disclosed in the U.S. patent application Ser. No. 11/533,304, filed on Sep. 19, 2006.

A typical procedure of imaging the gastrointestinal tract based on a wireless capsule camera consists of an inpatient visit in the morning during which a clinician attaches the base station apparatus to the patient and the patient swallows the capsule. The system records images beginning just prior to swallowing and records images of the gastrointestinal (GI) tract until its battery becomes fully discharged. For the system based on an autonomous capsule camera, the images captured will be stored in on-board memory and there is no need to attach a base station to the patient. After the capsule camera is swallowed, peristalsis propels the capsule through the GI tract. The rate of passage depends on the degree of motility. Usually, the small intestine is traversed in 4 to 8 hours. It takes longer to travel through the entire GI tracts. In order to reduce the procedure time for examining the colon, medication is needed to increase the transit speed. Some patients have known slow transit speed and in general the transit time is even long while a patient is sleeping. It is desirable that a means for reducing the procedure time by applying an electrical stimulus to the capsule in vivo. While the capsule camera usually moves in the forward direction (i.e., toward the rectum), it may undergo a retrograde motion occasionally, particularly in the colon. Furthermore, the capsule camera may stay at one place for certain periods of time. Beside the capsule camera, there are other in vivo capsule devices used for various diagnosis and treatment purposes. Other capsule devices also encounter the same issue as the capsule camera. It is desirable to provide an apparatus and method to influence the movement of the capsule device in the GI tract. The capability to influence the movement of the capsule device may offer benefits to broad applications associated with a capsule device.

BRIEF SUMMARY OF INVENTION

A capsule endoscopic device with movement control is disclosed. The capsule endoscopic device comprises a capsule housing, one or more electrodes disposed fixedly through the capsule housing, a signal generation/signal driver unit, an interface circuit and a switch module. The electrodes apply electrical stimulus to living body tissue in a patient's gastrointestinal tract. The signal generation/signal driver unit generates the electrical stimulus for the electrodes. The switch module is coupled to the electrodes, the signal generation/signal driver unit and the interface circuit. Furthermore, the switch module is configured to connect the electrodes to the signal generation/signal driver unit or the interface circuit depending on an operation mode. The switch module, the signal generation/signal driver unit and the interface circuit are inside the capsule housing.

When the capsule endoscopic device is set to a capture mode, the switch module is configured to connect the electrodes to the signal generation/signal driver unit during the capsule endoscopic device travels through the patient's gastrointestinal tract. When the capsule endoscopic device is set to a download mode, the switch module is configured to connect the electrodes to the interface circuit after the capsule endoscopic device exits from a patient's body. The interface circuit retrieves the image data and/or other sensing data stored in a memory inside the capsule housing and provides the image data and/or other sensing data to the electrodes. The memory may correspond to an archival memory.

The capsule endoscopic device may further comprise a signal processing circuit inside the capsule housing, and the signal processing circuit is coupled to the switch module and a second memory. The capsule endoscopic device can be set to a data collection mode and the switch module is configured to connect the electrodes to the signal processing circuit during the capsule endoscopic device is travels the patient's gastrointestinal tract and the signal processing circuit collects electrochemical parameters through the electrodes. The electrochemical parameters are stored in the second memory and the second memory may correspond to a second archival memory. The electrochemical parameters and the image data and/or other sensing data can be stored in a same archive memory.

DETAILED DESCRIPTION OF THE INVENTION

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. Reference throughout this specification to "one embodiment," "an embodiment," or similar language means that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

Figure 1A:
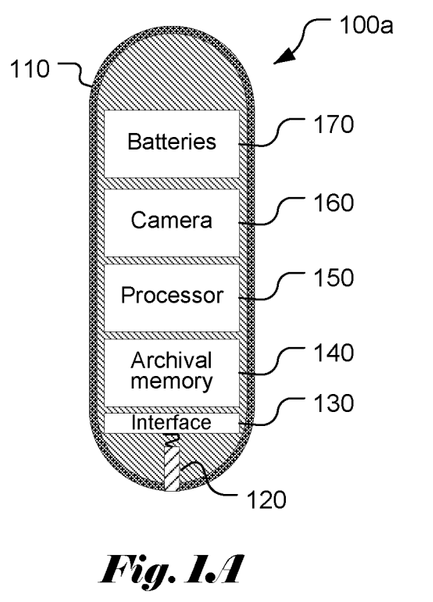
FIG. 1A-FIG. 1D illustrate four examples of electrode arrangement for the capsule device incorporating an embodiment of the present invention.

In an embodiment according to the present invention, the capsule incorporates an electrical terminal, where the electrical terminal is electrically connected to a circuit inside the capsule housing. The electrical terminal is also called an electrode. FIG. 1A illustrates an example of a capsule device 110 incorporating an embodiment of the present invention. The capsule device usually has an elongated shape having two ends in the longitudinal direction. In FIG. 1A, the electrical terminal or electrode is in the form of a stud 120, where the end of the stud facing toward outside of the capsule has a surface that is flush with the capsule housing, as shown in FIG. 1A. However, the stud need not be exactly flush to the housing outer surface as long as their recess or protrusion is small and the outer surface of the capsule, including the studs, is smooth. The capsule device shown in FIG. 1A corresponds to a capsule camera. Nevertheless, an embodiment according to the present invention may be incorporated in other capsule devices as well. In the example of FIG. 1A, the capsule device also includes archival memory 140, processor 150, camera 160, and batteries 170. The archival memory is used to store captured images. However, the archival memory may also be used to store other sensory data (such as temperature and PH values). If a wireless capsule camera is used, a wireless transmitter or a wireless transceiver (transmitter and receiver) is used. For the wireless capsule camera, the archival memory may not be needed or may be reduced. The camera typically comprises an image sensor (such as a CMOS or CCD image sensor), an optical system (not shown in FIG. 1A) to project an object in the field of view onto the image sensor, and image processing and compression module. The processor 150 may be used to support the image processing and compression functions and the compression functions may comprise motion-compensated video coding. Furthermore, the processor 150 may also be used to support other functions such as light control for LED light (not shown in FIG. 1A). While a processor module 150 is shown in FIG. 1A, the processor module may also be implemented using multiple processors and also may be physically separated into multiple modules.

Figure 1B:
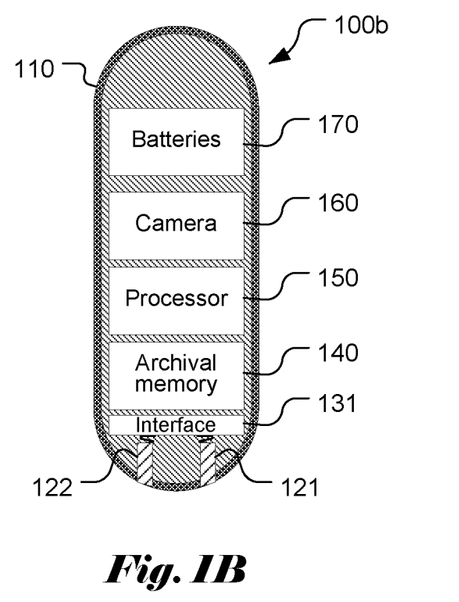
Figure 1C:
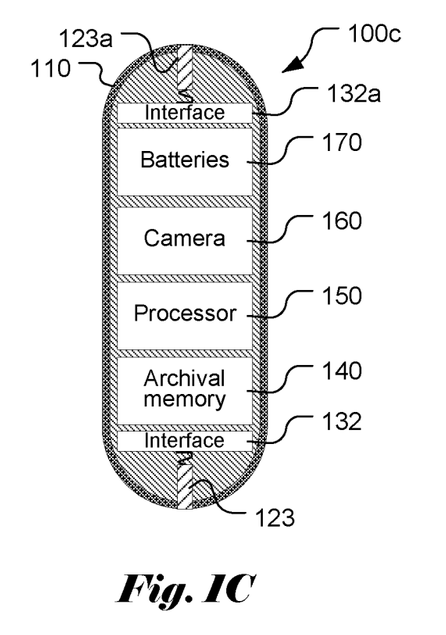
Figure 1D:
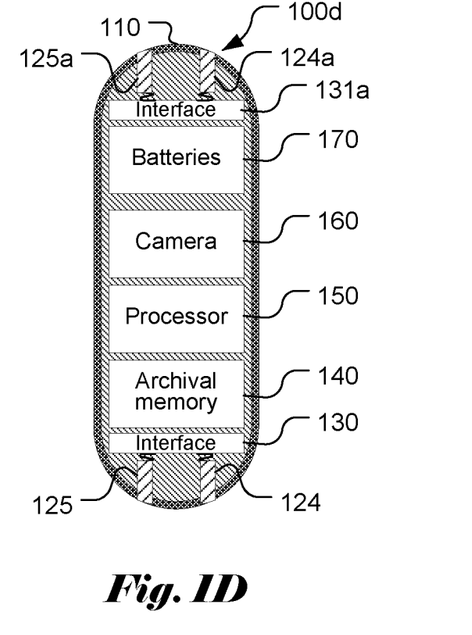

While FIG. 1A illustrates an example of a single electrode incorporated in a capsule device to practice the present invention, a capsule device may also incorporate more than one electrode in the capsule device to practice the present invention. For example, FIG. 1B illustrates an example of a capsule device with two electrodes (121 and 122) at one end of the capsule device. Furthermore, a capsule device may also incorporate one or more electrodes on both ends. For example, FIG. 1C illustrates an exemplary capsule incorporating an electrode on each end of the capsule (123 and 123a) and FIG. 1D illustrates an exemplary capsule incorporating two electrodes on each end of the capsule (124, 125, 124a and 125a).

Figure 2A:
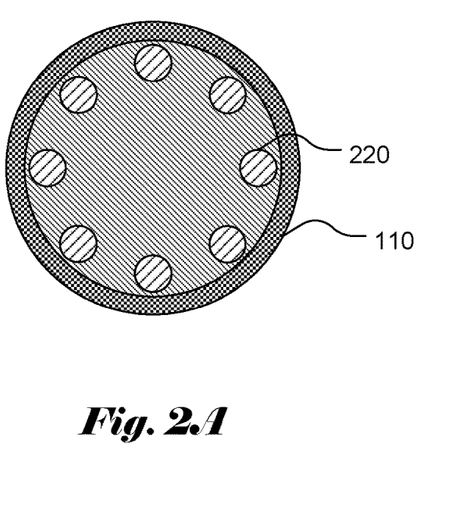
FIG. 2A illustrates an example of multiple electrodes configured in a circle at one end of the capsule device in the longitudinal direction.
Figure 2B:
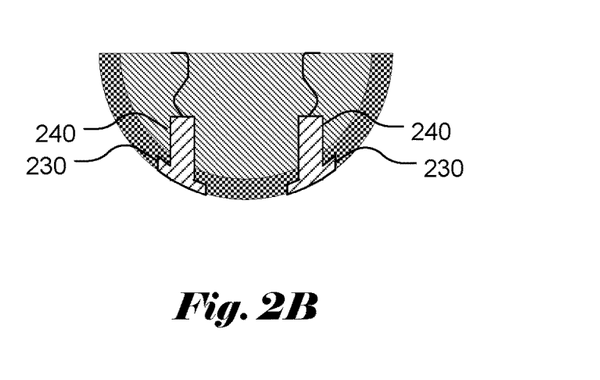
FIG. 2B illustrates an example of electrode structure having an area of conductive surface disposed on the surface of one end of the capsule device in the longitudinal direction.

In one implementation, multiple electrodes may be configured around the longitudinal axis on one end of the capsule symmetrically, such as in a circular arrangement. The plane associated with the circle is preferred to be perpendicular to the longitudinal axis of the capsule to increase the chance that the electrodes will touch the mucosal surface. For example, FIG. 2A illustrates a bottom view of a capsule device incorporating 8 electrodes (220) at one end of the capsule camera, wherein the electrodes are configured in a circle and the plane of the circle is perpendicular to the longitudinal axis of the capsule device. While the circle is used as an example of electrode configuration to increase the chance that one or more electrodes will touch the mucosal surface, other configurations that dispose the electrodes around the perimeter of one end of the capsule device will serve the same purpose. In another implementation, an electrode may comprise an area of conductive surface 230 which is disposed on the surface of one end of the capsule device as shown in FIG. 2B. Each electrode also comprises a stud portion 240 that is used as feed-through portion to provide support for the conductive surface portion as well as to provide conductive connection from the conductive surface to other components inside the housing 110. The conductive surface (230) shown in FIG. 2B has a larger cross section to improve the chance of making contact with the mucosal surface. Nevertheless, the conductive surface 230 portion of the stud may be formed by extending the feed-through portion through the capsule housing and having the exposed end of the feed-through portion flash with the housing surface substantially. In U.S. Provisional Patent Application, Ser. No. 61/657,747, filed on Jun. 9, 2012, a connector arrangement for a capsule device is disclosed and the connectors can be used as the electrodes to practice the present invention.

In yet another implementation, an electrode is implemented with an area covered by traces of conductive surface material. These conductive traces are connected to other components or contact points inside the capsule via a conductive part such as a metal stud or a metal wire. The electrode may be connected to an internal signal or stimulus sources via the conductive part. In one implementation, feed-through is used to connect the internal circuit to the external terminal or electrode. The implementation of feed-through needs to maintain the hermetic seal of the capsule. In one example, adhesive is applied and cured to provide the seal.

An embodiment of the present invention configures one or more electrodes for multiple functions. For example, the electrode may be coupled to the storage device within the capsule to download data after the capsule is excreted from the human body. Furthermore, the electrode may also be used to exert electrical stimulus in vivo to stimulate the intestine muscle contraction to change motor activity and to cause the capsule to move faster or slower, or change direction of the movement. Therefore, the electrodes may be configured to provide the function of in vivo data transmission using the human body as an electrical media, where an electrical signal may be exerted on the electrodes to send signal to an external device coupled to the human body. The electrodes may also be configured to provide sensing function such as measuring electrochemical parameters within the GI track.

The electrodes can be coupled to a processing unit to provide the signal required to drive the electrodes or to process the signal sensed by the electrodes. The processing unit may be implemented in a state machine and a circuit module comprising logic circuits and/or controller. Furthermore, the electrodes may be coupled to a switching circuitry, where the switching circuitry may configure the electrodes to perform a desired function from a set of functions. For example, the electrodes may be configured to perform movement adjustment function when the capsule is inside the GI tract. While the capsule device is inside the human body, the electrodes may be configured, by time sharing with the movement adjustment function, to collect electrochemical data in the GI tract. Alternatively, multiple sets of electrodes can be used for concurrent movement adjustment and electrochemical data collection. Furthermore, the electrodes are configured to perform data download function after the capsule device exits from the human body. A system incorporating an embodiment of the present invention may comprise a switch module that selectively connects the electrodes to a respective module to perform the selected function. The modules performing various functions may be implemented on separate modules with respective processor and respective analog driving circuitry. Some of the separate modules may share some common components. Furthermore, the modules may also be implemented as a single integrated module. In one embodiment a programmable processor could perform different functions with different embedded firmware codes.

Figure 3:
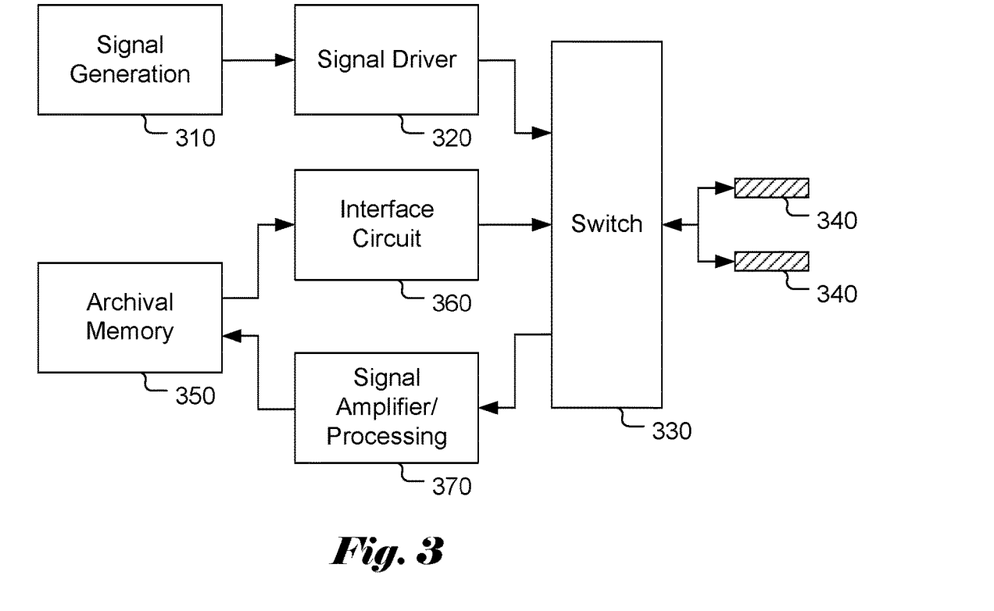
FIG. 3 illustrates an exemplary block diagram of a capsule device incorporating multi-function electrodes according to an embodiment of the present invention.

FIG. 3 illustrates a simplified example of three-function electrode for movement adjustment, data collection and data download. During movement adjustment function, the required signal for the electrodes is generated by signal generation module 310. In order to effectively adjust the capsule movement, the signal delivered to the electrodes may have to be brought to a certain voltage level or current level. The signal driver 320 is used to form the desired signal level for the electrodes 340. Two electrodes are shown in the example. However, more or less electrodes may be used. The switch 330 is used to properly connect a corresponding module to the electrodes. The switch 330 may be controlled by a controller or a system processor which is not shown in FIG. 3. While single lines are connected between various modules and the electrodes, each single line may represent multiple wires as appropriate. The movement or pose adjustment can cause the capsule device to move faster or slower, or to change direction or orientation to achieve better image capture during the capture mode.

In the data collection mode, the electrodes are connected to the signal amplifier/processing module 370 to gather the electrochemical data and stored in archival memory 350. In the data download mode, the data stored in the archival memory 350 is read out into the interface circuit 360 and the module is coupled to the electrodes 340 so that an external device may access data stored inside the capsule device through the electrodes 340 without the need to physically open the capsule device. FIG. 3 is intended for an illustration of an embodiment of the present invention, a person skilled in the art may practice the present invention with other variations without departing from the spirit of the present invention. While a single archive memory is shown in FIG. 3, separate archive memories may also be used for sensory data collection and image capture.

The capsule device is typically in an elongated shape so that the capsule device will travel primarily along the longitudinal direction. However, it is uncertain regarding which end of the capsule will be facing the forward direction when moving along the GI tract. Therefore, when a stimulus signal is applied to the electrode for adjusting the capsule movement, the capsule device may be inadvertently moved in a wrong direction. An embodiment according to the present invention incorporates a set of electrodes on each end of the capsule device and a direction determination module to determine the direction of the capsule device in the GI tract. Upon the direction determined and the desired movement adjustment, the system embodying the current invention may configure the capsule device to apply correspond stimulus signals to the electrodes. For example, if a movement adjustment to cause the capsule device move forward is desirable, a stimulus signal can be applied to the electrodes at the end of the capsule device corresponding to the backward end. The signal from the electrodes will stimulate the mucosal surface and cause it to contract. The capsule will move in the forward direction due to the intestine contraction caused by the electrical stimulus. When a stimulus needs to be applied to one end of the electrodes, the electrodes at the other end can be tri-stated, kept open, or high input/output resistance. In one embodiment, another set of switch may switch stimulus to either end of capsule.

In one embodiment of the present invention, the capsule device incorporates LED lights on four sides or more to illuminate the intestine wall. Based on light intensities received from different sides of the capsule, it can determine which side of the capsule is closer to the intestine wall. Alternatively, pose position derivation can be used to determine which side of the capsule is closer to the intestine wall. Accordingly, the electrodes on one side may be applied stronger or weaker stimulus than the other side at the same end of the capsule to steer the capsule into a desirable pose position.

In one embodiment according to the present invention, a capsule camera is used as the capsule device and the capsule camera direction inside the GI tract is determined according to images captured by the capsule camera. Furthermore, motion estimation can be used to determine motion information associated with the capsule, such as capsule direction, capsule displacement, capsule movement or any combination. The motion estimation can be derived based on a subset of the images, such as spatially and/or temporarily sub-sampled images, or cropped images. Global motion estimation can be used to determine the direction of movement. Since the capsule device moves primarily in a forward direction in the GI tract, the global motion can discern the direction of capsule device movement. Motion information such as motion vectors of a plurality of blocks could be used to determine the direction of the global motion. The average of these motion vectors, the mean, or the majority of these motion vectors, the peak of the histogram of these motion vectors, the median of the motion vectors, etc., can be used to determine the direction of the capsule device inside the GI tract.

To increase the accuracy in determining the direction of the capsule device inside the GI tract, the global motion vectors derived from images captured at different times over a time period can be used jointly to determine the direction of the capsule device inside the GI tract. For example, the average, mean, the majority of sign, the histogram, of the global motion vectors corresponding to images captured at different times over a time period can be used jointly to determine the direction of the capsule device inside the GI tract. Sometimes the capsule device may travel sideway, i.e., the axis of the capsule device corresponding to elongated direction is perpendicular to the longitudinal direction of the GI tract. The benefit of direction determination based on multiple global motion vectors over a period of time becomes apparent in this case. In one embodiment according to the present invention, no stimulus is exerted on the electrodes when decision of capsule direction inside the GI tract cannot be decided. The process of determining capsule direction inside the GI tract based on images captured can be made in vivo by the capsule device or externally by an external device such as a base station. For a wireless capsule camera without on-board storage for image data, the captured images are transmitted to the base station through the wireless link. In such case, the process of determining capsule motion information such as direction, displacement and speed inside the GI tract can be made at the base station. The decision on capsule direction inside the GI tract can be communicated back to the capsule through the wireless link. The capsule camera can apply the stimulus signal to the electrodes according to the information received from the base station.

Figure 4:
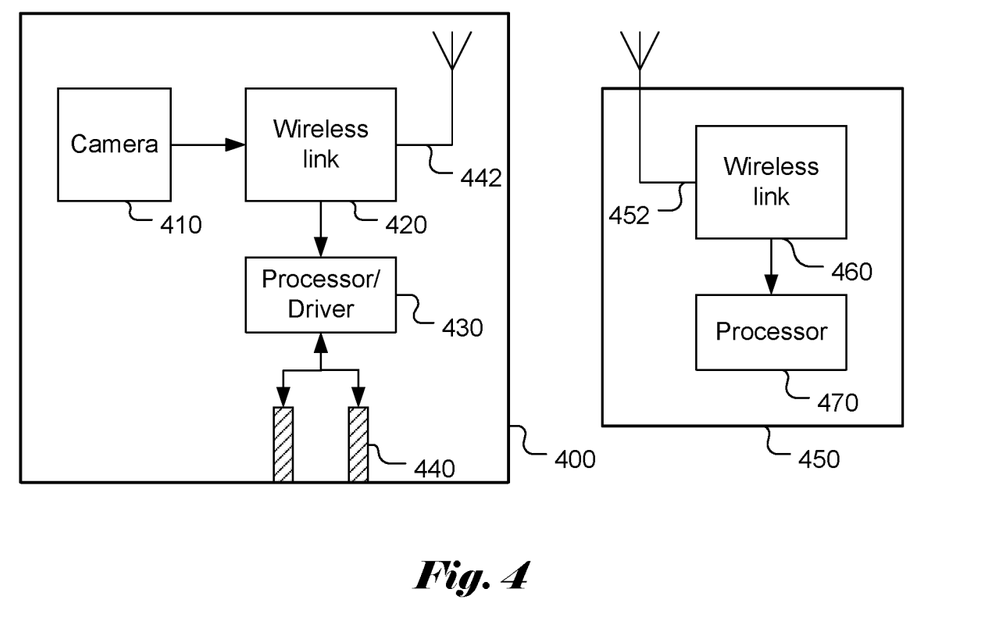
FIG. 4 illustrates an exemplary block diagram of a wireless capsule camera system using a base station to detect the capsule motion information or direction inside the GI tract.

An exemplary block diagram is shown in FIG. 4 to illustrate a capsule camera 400 and a base station 450 incorporating an embodiment of the present invention. The capsule camera 400 comprises camera 410, wireless link 420, processor/driver 430, electrodes 440 and antenna 442. The function of processor 430 can be shared with the processor inside camera 410 or wireless link 420. For example, process 430 may include motion estimation function which can be shared by motion estimation required by video compression in camera 410. Camera 410 captures images and the captured images are transmitted using wireless link block 420 and antenna 442. Base station 450 receives the captured images through antenna 452 and wireless link 460. The received images are processed by processor 470, where motion information such as the capsule direction with respect to the GI tract is determined. The information of the determined capsule direction with respect to the GI tract is transmitted back to the capsule camera. The capsule camera can determine the needed stimulus signal according to the determined capsule direction and the desired movement adjustment. Alternatively, processor block 470 at base station 450 may further determine a control signal based on the determined capsule direction and the desired movement adjustment and transmit the control signal to the capsule camera through wireless link 460. FIG. 4 is intended for illustration of an embodiment of the present invention, a person skilled in the art may practice the present invention with other variations without departing from the spirit of the present invention.

When the capsule device travels inside the GI tract, the differences in transit time through the intestine among people are widespread. On one hand, when the capsule device moves too slowly inside the GI tract, it may be desired to increase the transit speed in the forward direction. On the other hand, when the capsule device moves too fast inside the GI tract, it may be desired to decrease the transit speed in the forward direction. When stimulus is needed to adjust the capsule device movement, the capsule direction inside the GI tract has to be known before the stimulus signal is applied. The motion vector-based direction determination may be used to determine the capsule direction inside the GI tract. Sometimes different sections of GI tract of the same person may have different transit speeds and the stimulus is needed in some part of the intestine to increase or to decrease the speed. In some sections of the GI tract, it may be preferred to have more images taken per distance travelled. Therefore, the control for adjusting capsule device movement may be different for different sections of the GI tract. The control for adjusting the capsule device movement may include criteria regarding when to apply the stimulus and the strength or length of the stimulus signal. Since the control for adjusting capsule device movement may be dependent on particular sections of the GI tract, such as the colon section and the small bowel section, the system may need to discern the different sections of the GI tract. In one embodiment of the present invention, the ratio of light intensity from the light sources versus the pixel values received by the image sensor is used to determine the different sections of the GI tract.

When the capsule device is a capsule camera, the images captured by the capsule camera can be used to discern the speed of the capsule device In this case, the image sensor inside the capsule device, which forms an integral part of a capsule camera, is used as the sensing device for determining the capsule direction inside the GI tract. As mentioned before, motion estimation may be used to determine the capsule movement between captured images. The distance travelled by the capsule camera can be divided by the corresponding time interval to determine the transit speed. In another embodiment, an accelerometer is incorporated inside the capsule as a sensing device to decide the speed of the capsule device. The integration of acceleration over time is used to measure the speed of the capsule device. Furthermore, the speed, in turn, can be integrated to derive the distance. In this case the speed of transit can be determined.

If the measured speed is different from a desired speed, the stimulus signal can be applied to the electrodes of the capsule device to adjust the speed.

In order to properly control the movement of the capsule device, the strength, duration and frequency of the stimulus have to be determined on the fly. For different individuals, the required strength and frequency of the stimulus to cause desired capsule movement may be different. Therefore, the strength and frequency of the stimulus is determined adaptively based on the responses of individuals to the applied stimulus according to an embodiment of the present invention. For example, if a stimulus applied does not cause anticipated motor activity or transit speed change, then the control module may increase the intensity of each application of the stimulus or increase the duration of each application of the stimulus. Alternatively, the control module may increase the frequency of the applying the stimulus. For safety reason, there is an upper limit on the strength of the stimulus. In one embodiment adjusting duty cycle or pulse width modulation is used to control speed.

The bowel transit is episodic in nature and the need to apply the stimulus may be made on a longer period of time according to a predetermined schedule and/or location. For example, it may take about 4 hours for a capsule device to reach the cecum after the device is swallowed, or it may take the capsule device 10 hours to travel about 5 meters to reach the cecum. Accordingly, the capsule device may be configured to activate the movement adjust function upon a predetermined schedule or when the capsule device reached the intended location. The stimulus strength and duration will be adapted to the individual as well as the specific section of GI tract to achieve desired response of motor activity. In one embodiment the stimulus is applied simply after certain hours, for example 8 hours.

Figure 5:
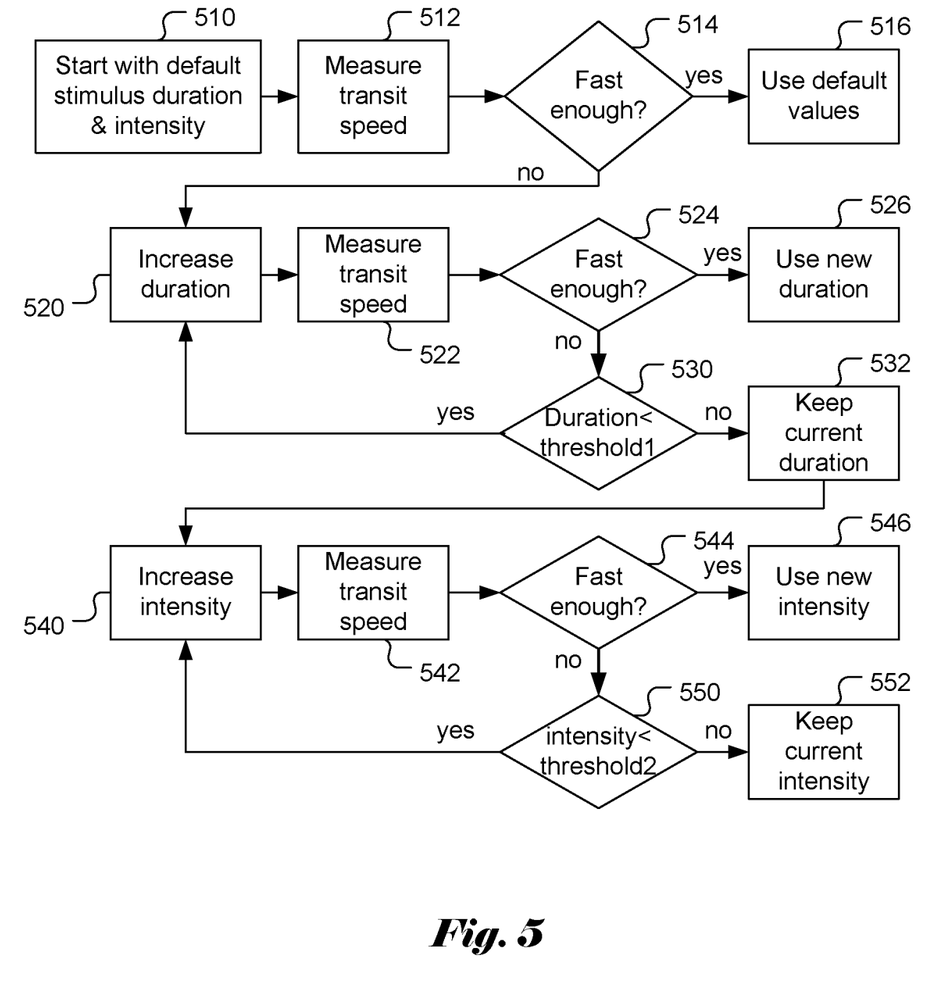
FIG. 5 illustrates an exemplary flow chart for a system incorporating an embodiment of the present invention, where the stimulus duration and intensity are adjusted separately.

FIG. 5 illustrates an exemplary flow chart for adaptively determining the intensity and duration of the stimulus. The decision is based on the transit speed, where the desired transit speed may be dependent on the particular GI sections. For example, if the capsule device is intended to collect more sensing data in the small intestine section, then it may be desirable to cause the capsule device to travel slower in the small intestine section. In FIG. 5, the initial control is according to block 510 and then the transit speed is measured in block 512. As mentioned previously, the transit speed can be measured based on motion vector over a period of time, where the global motion vectors in the longitudinal direction of the GI tract are used to estimate the distance travelled by the capsule device and the speed can be determined by dividing the estimated distance by the corresponding total time interval. The measured speed is compared with a target speed in block 514. If the speed is fast enough, then the default stimulus duration and intensity are maintained as shown in block 516. If the speed is not fast enough, then the stimulus duration is increased as shown in block 520. After the duration is increased in block 520, the transit speed is measured again in block 522 and compared with the desired transit speed in block 524. If the speed is fast enough, then the increased stimulus duration is used as shown in block 526. If the speed is not fast enough, then the stimulus duration is compared with threshold 1 as shown in block 530. If the stimulus duration is less than threshold 1, the process goes back to block 520 to further increase the stimulus duration. Otherwise, the stimulus duration is not changed (block 532) and instead, the stimulus intensity is increased in block 540. After the intensity increases, the transit speed is measured again in block 542 and compared with the desired transit speed in block 544. If the speed is fast enough, then the increased stimulus intensity is used as shown in block 546. If the speed is not fast enough, then the stimulus intensity is compared with threshold 2 as shown in block 550. If the stimulus intensity is less than threshold 2, the process goes back to block 540 to further increase the stimulus intensity; otherwise, the stimulus intensity is not changed (block 552).

Figure 6:
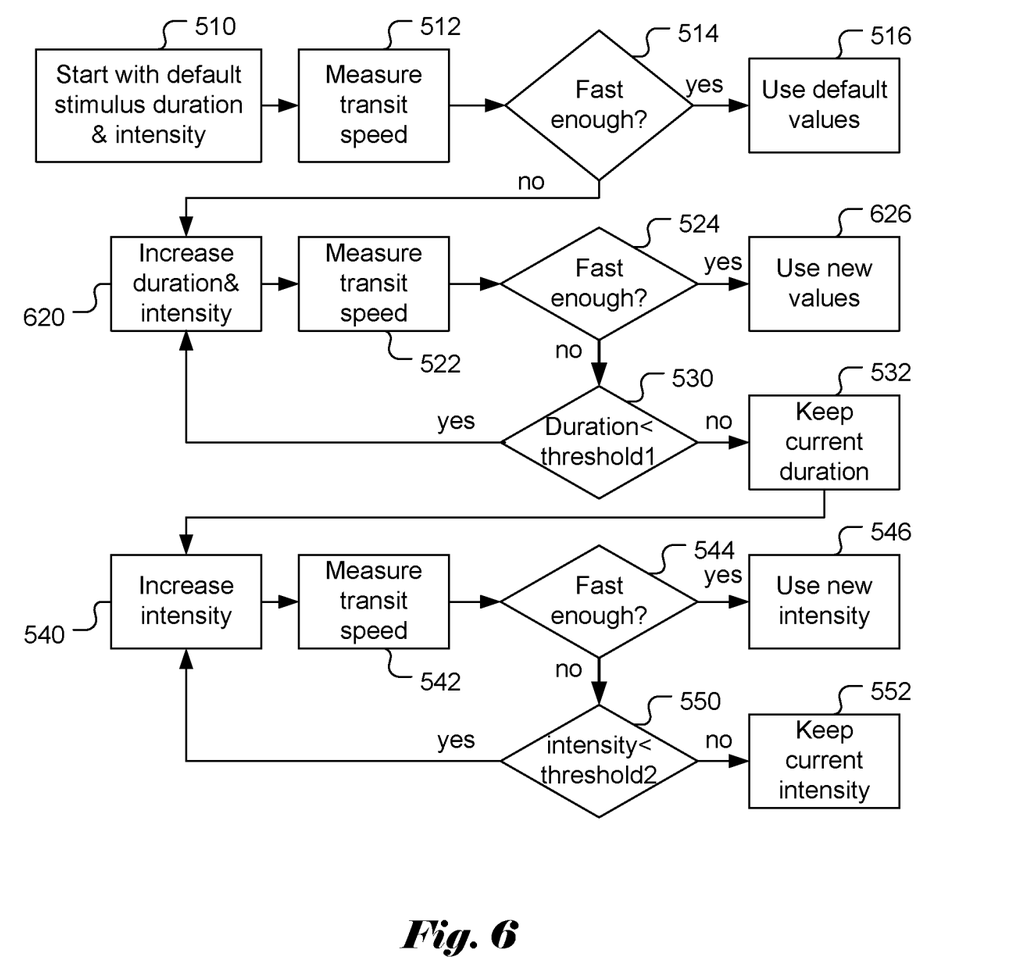
FIG. 6 illustrates an exemplary flow chart for a system incorporating an embodiment of the present invention, where the stimulus duration and intensity are adjusted simultaneously in one phase and separately in another phase.
Figure 7:
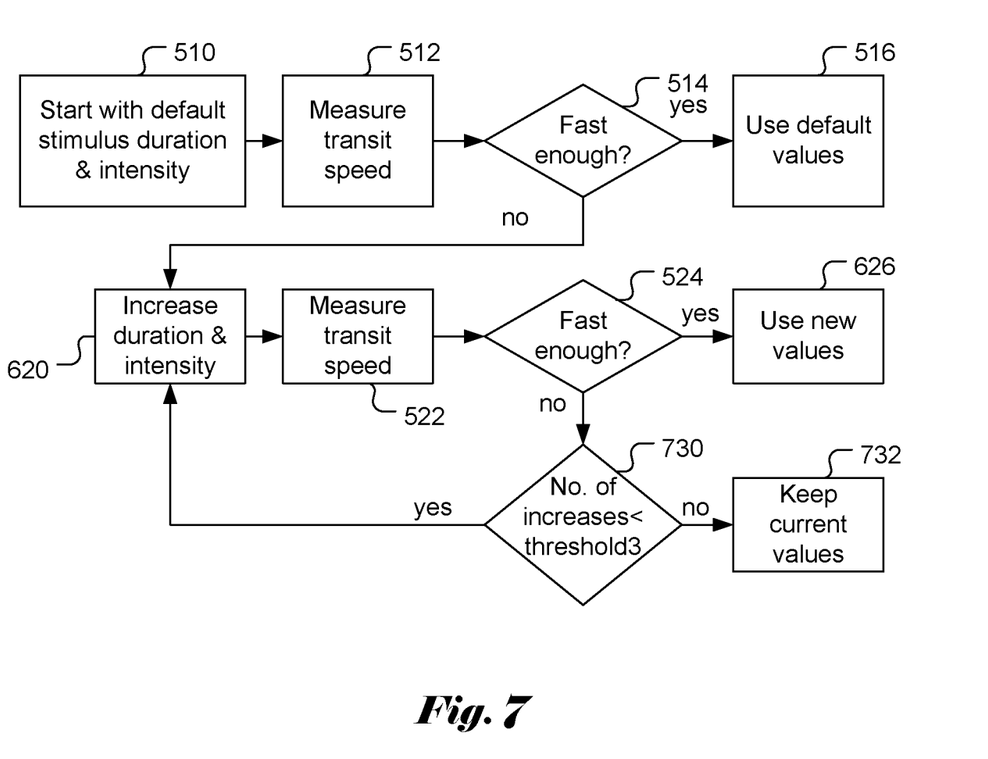
FIG. 7 illustrates an exemplary flow chart for a system incorporating an embodiment of the present invention, where the stimulus duration and intensity are adjusted simultaneously.

The flow chart in FIG. 5 illustrates one example to incorporate an embodiment of the present invention. A skilled person in the art may practice the present invention by rearranging the steps, adding more steps or removing some steps without departing from the spirit of the present invention. FIG. 6 illustrates another exemplary flow chart which is similar to the exemplary flow chart of FIG. 5. While block 520 of FIG. 5 only increases the stimulus duration, block 620 of FIG. 6 increases both the stimulus duration and intensity. If the measured speed is fast enough, both the increased duration and intensity values are maintained as shown in block 626. FIG. 7 illustrates an exemplary flow chart for a system incorporating another embodiment of the present invention. The system in FIG. 7 always increases the stimulus duration and intensity at the same time. The process associated with FIG. 7 is similar to the upper part of FIG. 6 except for blocks 730 and 732. In block 730, the number of increases is compared with threshold 3. If the number of increases is smaller than threshold 3, the process goes to block 620; otherwise the increased stimulus duration and intensity are maintained in block 732. In yet another example, the stimulus duty cycle can be adjusted instead of the stimulus duration and/or intensity. The intensity, duty cycle, and pulse width modulation may be used to control the capsule movement beside the stimulus duration.

As mentioned earlier that it may be desirable to cause the capsule device to travel slower in a section of the GI tract (e.g., the small intestine section) so that it can capture more images or collect more data in the GI tract. The exemplary movement adjustments as shown in FIG. 5 to FIG. 7 describe a process to apply stimulus to the electrodes to cause the capsule device move faster in the GI tract. A person skilled in the art can use similar process to cause the capsule device to transit at a slower speed. For example, if the transit speed measured is too fast, the duration, intensity, strength or any combination of them can be reduced to cause the capsule device to slow down. Furthermore, if the capsule device is equipped with electrodes on both ends, a stimulus signal can be applied to the electrode at the end that will cause the capsule device to slow down.

The process of determining the capsule direction inside the GI tract should be performed before the stimulus is applied to the electrodes. Consequently, there is a period of time that the capsule does not exert stimulus on the electrodes. This period of time for determining the capsule direction inside the GI tract is needed for the capsule device to gather multiple images and to make decision so as to be accurate and to avoid false determination causing the capsule to retrograde. Sometimes, the bowel activity is very low and this will make determination of the direction difficult. An embodiment according to the present invention may exert stimulus signals on both ends of the capsule (electrodes incorporated on both ends are assumed). The stimulus signals exerted on both ends of the capsule are substantially equal in intensity and duration in order to agitate the bowel momentarily. The stimulus signals can be applied to both ends substantially at the same time. The stimulus signals will trigger peristalsis to cause the capsule device to move by peristalsis. The direction detection can be performed and the determined direction can be used for capsule movement control by applying an appropriate stimulus to the electrodes at the correct end of the capsule. The series of process including initially applying the stimulus signal to cause the capsule device move due to agitated bowel, detecting the capsule direction and applying stimulus signal to cause a desire capsule device movement, is called stimulus decision mode. The process of capsule movement control, as described above, by exerting stimulus is always performed after the capsule direction is determined. However, the stimulus may also be applied while the decision is being made.

Due to the advancement in hardware technology, the size of capsule device may be further shrunk. When the small-size capsule device travels in a wider section of the GI tract, the capsule device may flip sometimes causing the forward end to become the rear end. Therefore, the decision regarding which end of the capsule is facing forward direction has to be made frequently. However, if the speed detection shows that the capsule moves at the desired speed during a period of time, then there is no need to perform direction detection and no stimulus is needed either.

For a very small capsule device, the capsule device tends to turn more easily. In order to detect the capsule device turn, pose estimation is utilized. The pose (i.e., the three dimensional position and orientation with respect to a coordinate system) of the capsule device can be estimated from images captured by the capsule device using pose estimation technique. Techniques for pose estimation are well known in the field of machine vision and the details are not repeated here. In an ideal case, the capsule longitudinal axis should be aligned with the axis perpendicular to the cross section of the GI tract and the capsule faces a forward direction. If the capsule tilts, there will be an angle between the two axes. The angle between the two axes can be determined from the pose of the capsule device. If the angle exceeds a threshold, it may be desirable to apply a stimulus to the capsule device to reduce the tilt so that the capsule device will not turn inadvertently.

For a wireless capsule device, the images can be transmitted to a base station so that the capsule pose information can be estimated at the base station. The estimated pose information can be transmitted to the capsule device so that the capsule device can adjust the speed and/or orientation according to the estimated pose information. Alternatively, the base station can determine the required control signal based on the estimated pose information and transmit the control information to the capsule device. If the capsule device uses on-board memory to store the captured images, the capsule device has to estimate the pose information using processor inside the capsule device.

For a wireless capsule, a gyroscope, accelerometer, or electron compass can be placed both within the capsule and on patient's body (such as the torso). Based on sensed information from the sensing device within the capsule device and on the patient's body, information regarding whether the capsule device turns can be made by a base station. Accordingly, the base station may transmit the control signal to the capsule device.

The above description is presented to enable a person of ordinary skill in the art to practice the present invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the above detailed description, various specific details are illustrated in order to provide a thorough understanding of the present invention. Nevertheless, it will be understood by those skilled in the art that the present invention may be practiced.

An embodiment of the present invention to perform the steps disclosed in this application can be based on an application specific integrated circuit (ASIC), a microcontroller, or a hardware-based processor. An embodiment of the present invention may also be program codes to be executed on a Digital Signal Processor (DSP) to perform the processing described herein. The invention may also involve a number of functions to be performed by a computer processor, a digital signal processor, a microprocessor, or field programmable gate array (FPGA). These processors can be configured to perform particular tasks according to the invention, by executing machine-readable software code or firmware code that defines the particular methods embodied by the invention. The software code or firmware code may be developed in different programming languages and different format or style. The software code may also be compiled for different target platform. However, different code formats, styles and languages of software code and other means of configuring code to perform the tasks in accordance with the invention will not depart from the spirit and scope of the invention.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A capsule endoscopic device comprising:
a capsule housing;
one or more electrodes disposed fixedly through the capsule housing;
a signal generation/signal driver unit to generate an electrical stimulus for said one or more electrodes;
an interface circuit to read or write image data and/or other sensing data stored inside the capsule housing; and
a switch module coupled to said one or more electrodes, the signal generation/signal driver unit and the interface circuit, wherein the switch module is configured to connect said one or more electrodes to the signal generation/signal driver unit to adjust capsule endoscopic device movement or pose by applying a stimulus to the capsule endoscopic device via said one or more electrodes in a first operation mode, and the switch module is configured to connect said one or more electrodes to the interface circuit to download stored data from a memory inside the capsule endoscopic device via said one or more electrodes in a second operation mode; and
wherein at least one of said one or more electrodes is configured to adjust the capsule endoscopic device movement or the pose in the first operation mode and to download stored data from the memory inside the capsule endoscopic device in the second operation mode; and
wherein the switch module, the signal generation/signal driver unit and the interface circuit are inside the capsule housing.

2. The capsule endoscopic device of claim 1, wherein the first operation mode corresponds to a movement adjustment mode and the switch module is configured in the first operation mode for adjusting capsule endoscopic device movement or pose when the capsule endoscopic device travels in patient's gastrointestinal tract.

3. The capsule endoscopic device of claim 1, wherein the second operation mode corresponds to a download mode and the switch module is configured in the second operation mode for data downloading from the memory to an external device after exiting from a patient's body.

4. The capsule endoscopic device of claim 3, wherein the interface circuit retrieves the image data and/or other sensing data stored in the memory inside the capsule housing and provides the image data and/or other sensing data to said one or more electrodes.

5. The capsule endoscopic device of claim 4, wherein the memory corresponds to an archival memory.

6. The capsule endoscopic device of claim 1 further comprising a signal processing circuit inside the capsule housing, wherein the signal processing circuit is coupled to the switch module and the memory.

7. The capsule endoscopic device of claim 6, wherein the second operation mode corresponds to a data collection mode and the switch module is further configured in the second operation mode for to gather electrochemical data of patient's gastrointestinal tract and to store collected data in the memory when the capsule endoscopic device travels in the patient's gastrointestinal tract.

8. The capsule endoscopic device of claim 7, wherein electrochemical data are stored in the memory.

\* \* \* \* \*